(12) United States Patent
Papouras et al.

(10) Patent No.: US 8,092,373 B1
(45) Date of Patent: Jan. 10, 2012

(54) ENDOSCOPE HAND ASSIST DEVICE

(75) Inventors: William C. Papouras, Akron, OH (US); Vall Iliev, Stow, OH (US)

(73) Assignee: William C. Papouras, Akron, OH (US)

( * ) Notice: Subject to any disclaimer, the term of this patent is extended or adjusted under 35 U.S.C. 154(b) by 759 days.

(21) Appl. No.: 12/196,027

(22) Filed: Aug. 21, 2008

Related U.S. Application Data

(60) Provisional application No. 60/970,970, filed on Sep. 9, 2007.

(51) Int. Cl.
*A61B 1/00* (2006.01)

(52) U.S. Cl. .................... 600/131; 600/102

(58) Field of Classification Search ............ 600/102, 600/104, 121–125, 131
See application file for complete search history.

(56) References Cited

U.S. PATENT DOCUMENTS

| | | | | |
|---|---|---|---|---|
| 4,886,049 | A | * | 12/1989 | Darras .................. 600/124 |
| 5,333,603 | A | * | 8/1994 | Schuman ................ 600/108 |
| 5,616,131 | A | | 4/1997 | Sauer et al. |
| 5,746,693 | A | | 5/1998 | Spitz et al. |
| 6,077,286 | A | | 6/2000 | Cuschieri et al. |
| 6,083,151 | A | | 7/2000 | Renner et al. |
| 6,237,192 | B1 | * | 5/2001 | Garrison et al. .......... 16/422 |
| 6,261,294 | B1 | | 7/2001 | Stihl et al. |
| 6,432,047 | B1 | | 8/2002 | Gust et al. |
| 6,436,122 | B1 | | 8/2002 | Frank et al. |
| 6,540,737 | B2 | | 4/2003 | Bacher et al. |
| 6,652,488 | B1 | * | 11/2003 | Cover et al. ............. 604/118 |
| 6,793,621 | B2 | | 9/2004 | Butler et al. |
| 6,960,163 | B2 | | 11/2005 | Ewers et al. |
| 2008/0064929 | A1 | * | 3/2008 | Wiedenbein ............ 600/131 |

OTHER PUBLICATIONS

Steven Frandzel; "The Perils of Endoscopy—Patients Are Not the Only Ones to Suffer Adverse Events"; Reprinted from Gastroenterology & Endoscopy News, Sep. 2005, 56:1, 16-17.
R. Buschbacher; "Overuse Syndromes Among Endoscopists"; Endoscopy 1994; 26: 539-544.
General Surgery News; "Caution: Endoscopy Can Be Hazardous to Your Health"; Issue: Oct. 2005; vol. 32:10.
General Surgery News; "A Surgical Option for Surgeons with Endoscopy-Induced Injury"; Issue Feb. 2006; vol. 33:02.

* cited by examiner

*Primary Examiner* — Matthew J Kasztejna
(74) *Attorney, Agent, or Firm* — John D. Gugliotta, Esq.

(57) ABSTRACT

An ergonomic holding assist device for endoscopes comprises an attachment mechanism to removably secure the hand assist device to an endoscope. An ergonomic component comfortably fills a space made between a naturally extended palm and the grip portion of the endoscope. A center plate sandwiched between the attachment mechanism and the ergonomic component provides an approximate ½-inch clearance to a top of the device so that the ergonomic component reaches a thenar crease of the palm more comfortably. The flexor tendon of the thumb is comfortably supported by the ergonomic component so that endoscope-work-related injuries are avoided.

10 Claims, 10 Drawing Sheets

ENDOSCOPE HAND ASSIST DEVICE

RELATED INVENTIONS

The present invention is a Continuation of U.S. Ser. No. 60/970,970 and it claims priority to that provisional's Sep. 9, 2007 filing date. The present specification furthermore incorporates all the subject matter of the '970 application as if the latter is entirely rewritten herein.

BACKGROUND OF THE INVENTION

1. Field of the Invention

The present invention relates to an ergonomic holding assist device for endoscopes and, more specifically, to a hand assist device that provides a means for a gastroenterologist to comfortably extend a palm outwards to manipulate an endoscope.

2. Description of the Related Art

Gastroenterologists and other surgical specialists perform endoscopies by utilizing an endoscope which requires they wrap their entire palm around a grip portion of the device. A very construction of the endoscope requires these specialists rotate the endoscope's pinwheels for prolonged periods, which is known to cause injuries from overuse. The very nature of the working position of the endoscope causes specialists, at minimum, to experience hand and wrist discomfort. It may furthermore cause some specialists either to experience symptoms similar to those of Carpal Tunnel Syndrome ("CTS") or to be diagnosed with tendonitis.

Tendonitis is a medical condition that can lead to a crippling pain in the thumb, the forearm, the shoulder, the elbow, the neck and the back. These chronic pains also cause many specialists to experience psychological distress. Most specialists suffer from these pains while performing endoscopies; the pains cause them to interrupt procedures to stretch and to relax. The slightest discomfort in a health specialist can compromise a procedure and cause a misdiagnosis in a patient. To relieve the risks of injuries, it is anticipated that the palm should be extended away from the grip section of the endoscope such that it can maintain a natural position. It is further anticipated that a risk of injuries can be avoided if the flexor tendon of the thumb is supported by a feature on an endoscope. The present invention is a removably attachable endoscope ergonomic hand assist device that comprises features that achieve these objectives.

The means known in the art to reduce the risk of endoscopy-related injuries are limited to the following suggestions: maintaining proper posture; stretching, resistance training; repositioning monitors; and, taking breaks between procedures. For the more serious injuries, conservative therapies remain the mainstay of treatment until a surgery is required. There is no known endoscope that alleviates the risk of these pains and there are no known devices that work with the flexible endoscopes that cause this pain. For these reasons, there exists a long felt need to reduce the risks of endoscope-related injuries by means of repositioning a specialist's grip on the endoscope to a more comfortable one. The present invention comprises such a means, wherein an ergonomic assist device is removably attached to the grip section of the control handle on a conventional endoscope. The assist device supports the flexor tendon of the thumb while also relieving the palm from maintaining a tight, wrapped grip.

SUMMARY OF THE INVENTION

It is an object of the present invention to provide a means to alleviate the risks of work related injuries caused by endoscopies.

It is an object of the present invention to achieve the foregoing by teaching an ergonomic hand assist device that removably attaches to conventional endoscopes.

It is an object that the hand assist device support the flexor tendon of the thumb so that a specialist's grip is repositioned to a more comfortable one.

It is a further object that the present hand assist device relieve a surgeon from the tight, wrapped grip currently necessary for properly manipulating an endoscope.

It is an object that the grip is replaced with one that is a more natural and comfortable one, wherein a palm remains extended.

It is envisioned that the foregoing is accomplished by means of a hand assist device comprising the following features: (1) an attachment mechanism to removably secure the hand assist device to an endoscope; and, (2) an ergonomic component to comfortably fill a space made between a naturally extended palm and the grip portion of the endoscope.

It is further envisioned that a center plate sandwiched between the two provide an approximate ½-inch clearance to a top of the device so that the ergonomic component thus reaches a thenar crease of the palm more comfortably.

It is a final object of the present invention to provide all of the advantages that the foregoing objects entail.

BRIEF DESCRIPTION OF THE DRAWINGS

The advantages and the features of the present invention are better understood with reference to the following and the more detailed description and the claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the Figures.

Figure 1:
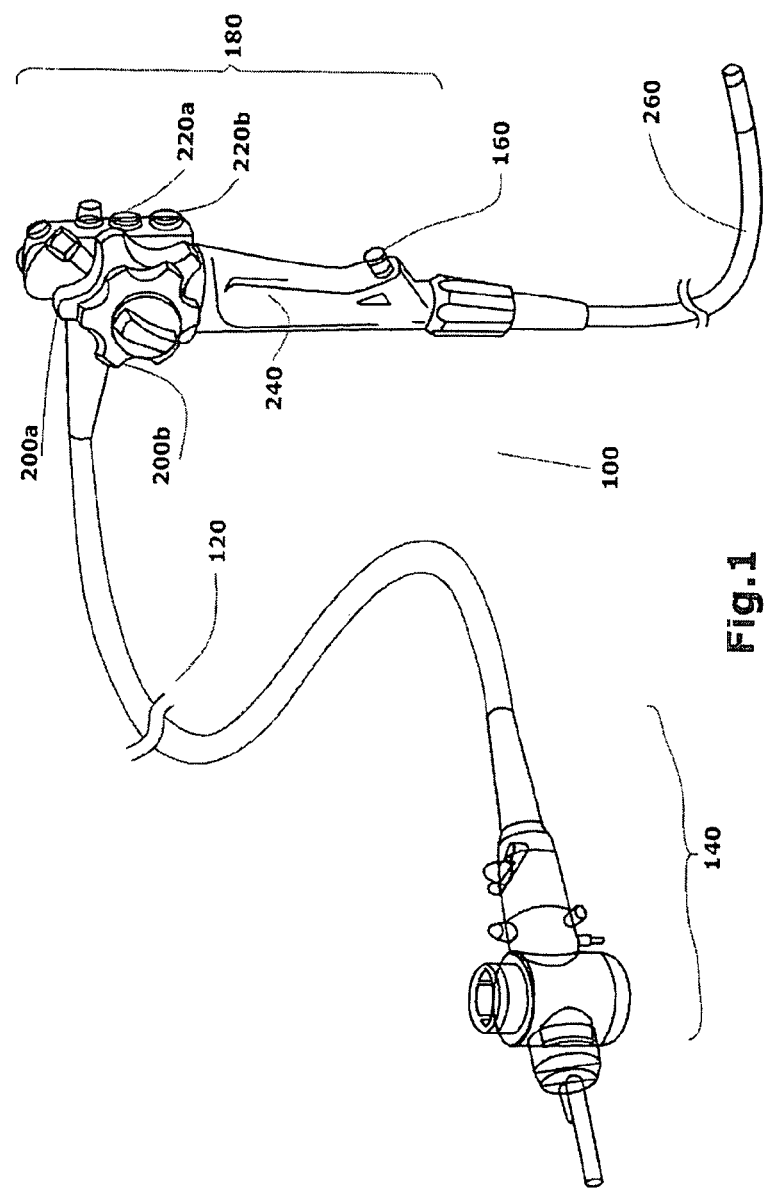
FIG. 1 is an endoscope known in the PRIOR ART, wherein a construction and a manner of utilizing the endoscope is shown.

In order to describe a complete relationship of the invention to the prior art, it is essential that some description be given to a construction and to a manner of utilizing a conventional endoscope 100. An endoscope is shown in FIG. 1 to essentially comprise a universal cord 120, a light delivery system 140, a lens, a rigid or a flexible tube 260 and a channel 160 for other medical devices. A gastroenterologist performs an endoscopy by grasping a control section 180, wherein a thumb is placed over the universal cord 120 to manipulate angulation control knobs 200a, 200b. An index finger is wrapped around the control section 180 to access a suction 220a and an air/water cylinder 220b. A middle, a ring and a pinky finger are wrapped around a grip section 240 of the control section 180 to further support the gastroenterologist's handle of the endoscope 100. The gastroenterologist's palm similarly wraps around this grip section 240 to manipulate the endoscope 100. The universal cord 120 can wrap over and be supported by a wrist.

1. Detailed Description of the Figures

Figure 2:
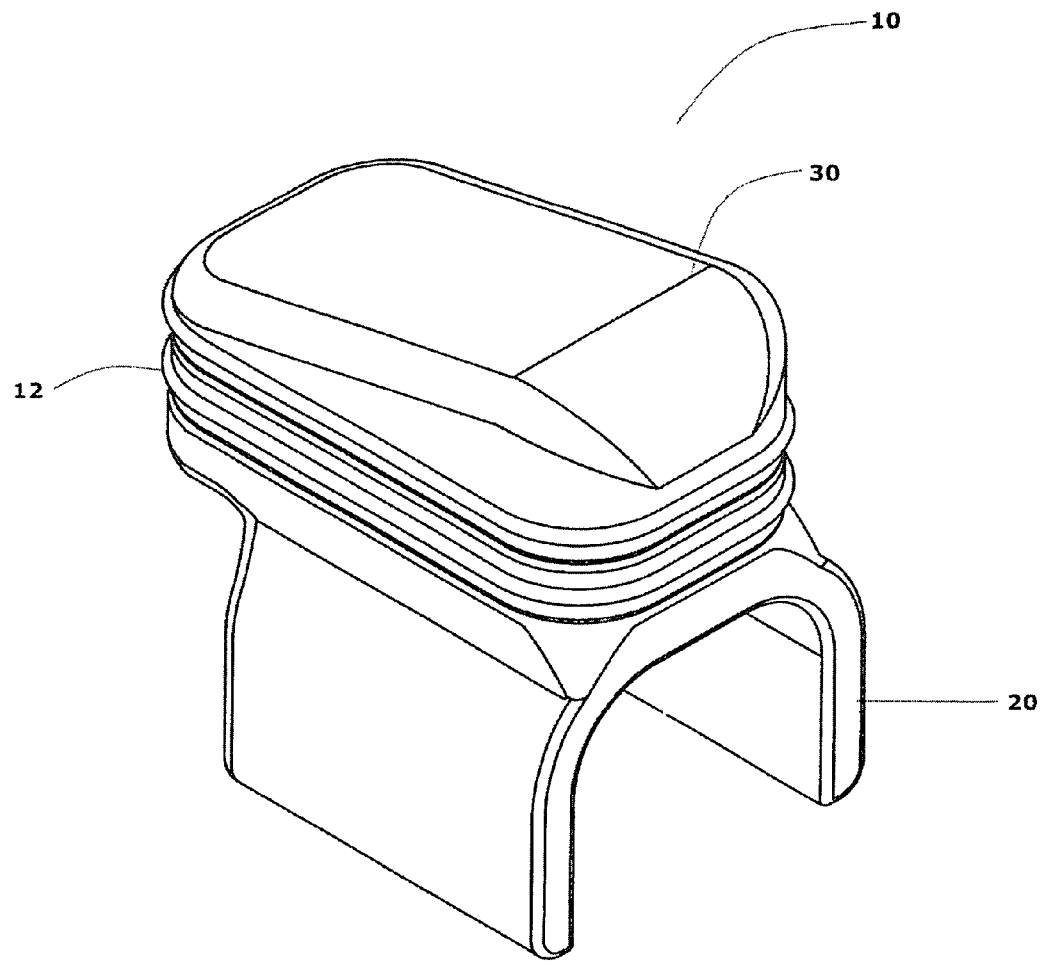
FIG. 2 is a first side elevational view of an endoscope ergonomic hand assist device according to a preferred embodiment of the present invention.
Figure 3:
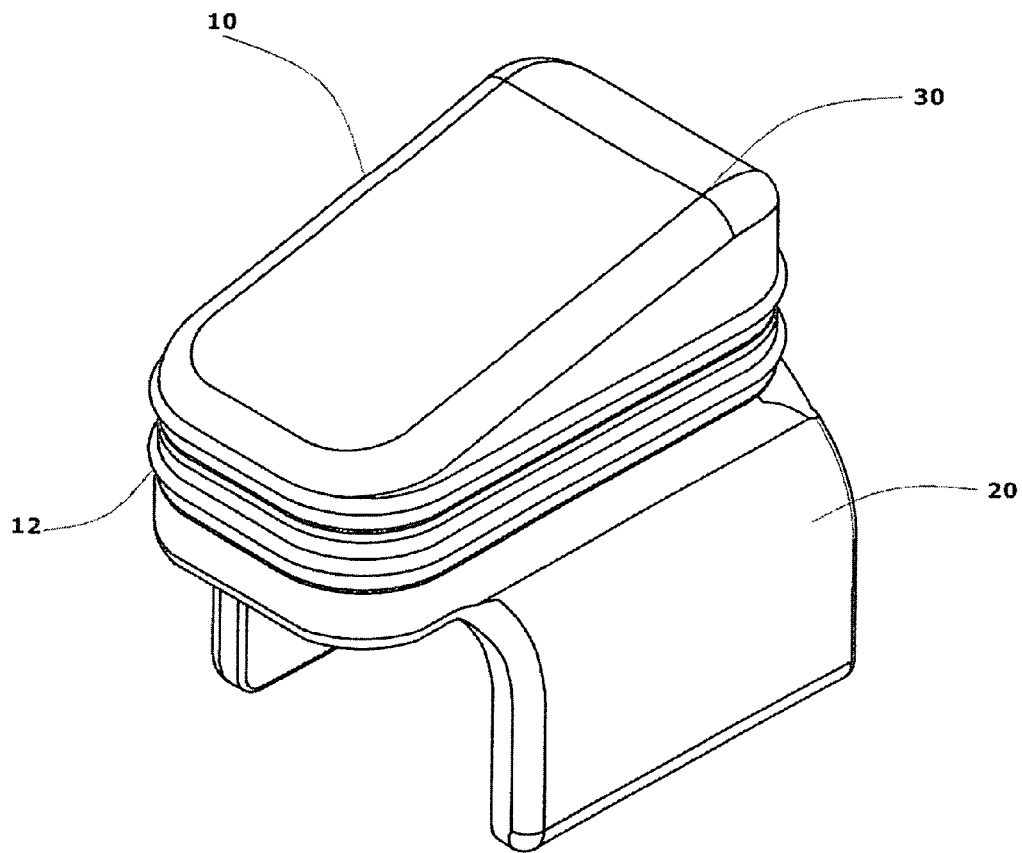
FIG. 3 is a second side elevational view of the hand assist device shown in FIG. 2.
Figure 4:
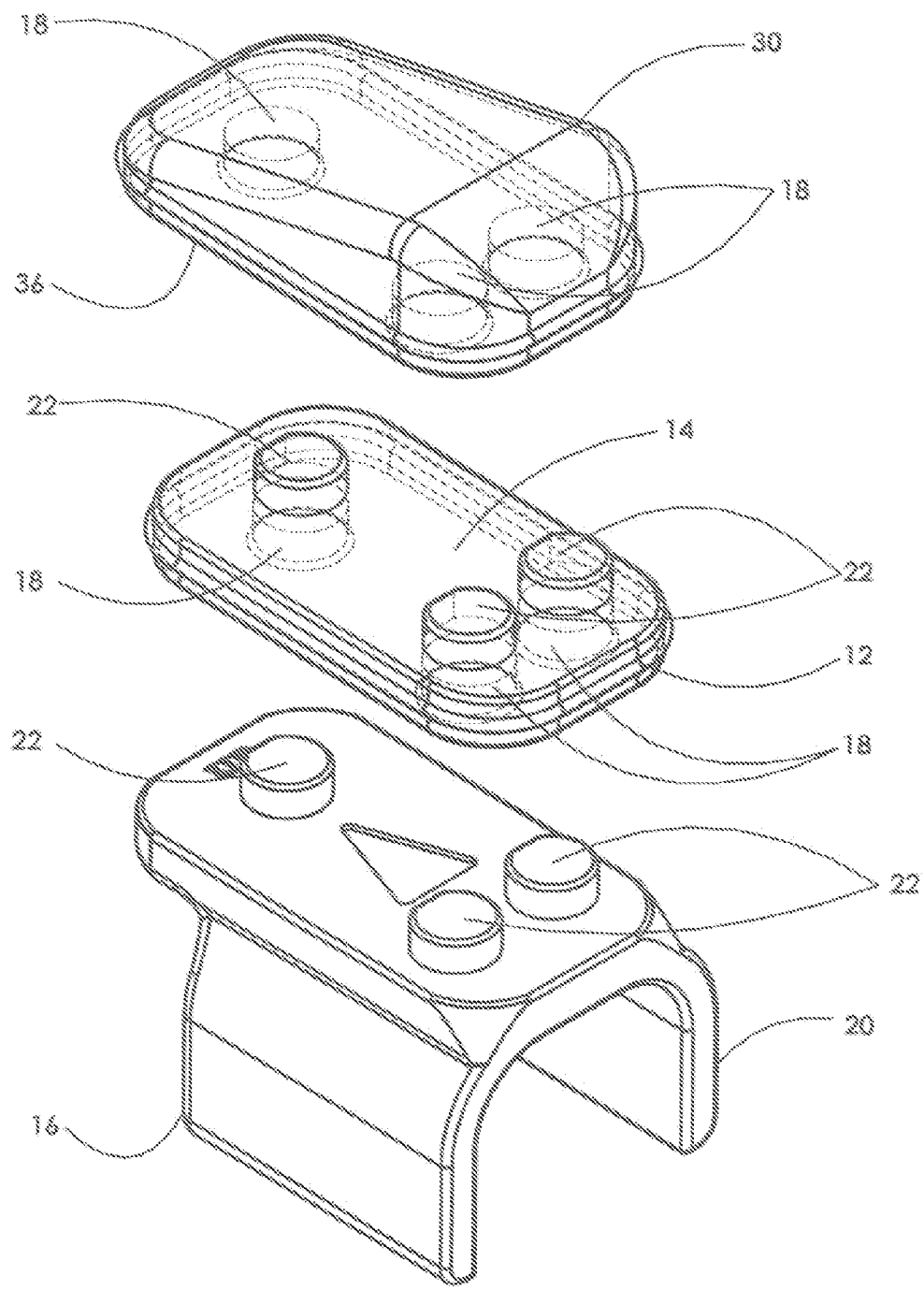
FIG. 4 is a partial exploded view of the hand assist device shown in FIG. 2.

It is anticipated that a gastroenterologist can work more comfortably, but without compromising the efficacy of an endoscopy, if his or her palm is capable of extending away from the grip section on the flexible endoscope to a more natural position. The present invention teaches a means to achieve this objective, wherein an ergonomic assist device is removably attached to the grip section of the control handle on a conventional endoscope. A preferred embodiment of the present endoscope ergonomic hand assist device (hereinafter referred to as "hand assist device") 10 is shown in FIGS. 2 and 3 to comprise an attachment mechanism 20, an ergonomic component 30 and a center plate 12. These components are shown with greater clarity in the partially exploded view of the device shown in FIG. 4.

The hand assist device 10 comprises a rectangular plate 12 which serves as a reference for an assembly of all the other components on the device. These components can be manufactured separately before they are assembled. The plate 12 comprises a top side 14 portion and an underside 16 portion. A plurality of depressions 18 are formed on the underside 16 to mate with the attachment mechanism 20. The underside 16 portion comprises three rounded depressions 18 that resemble cylindrical tubes; however, the numbers of, the shapes of and the depths of the depressions are not limited to those shown in the present drawing. The depressions 18 may rather comprise any number, shape or depth of tubes so long as they securely mate with corresponding studs 22 on the attachment mechanism 20. The topside 14 of the plate 12 comprises a plurality of studs 22 that are formed to mate with an ergonomic component 30. Similar to the limitations disclosed for the depressions 18, the studs 22 are not limited to any number shape or size.

Figure 5:
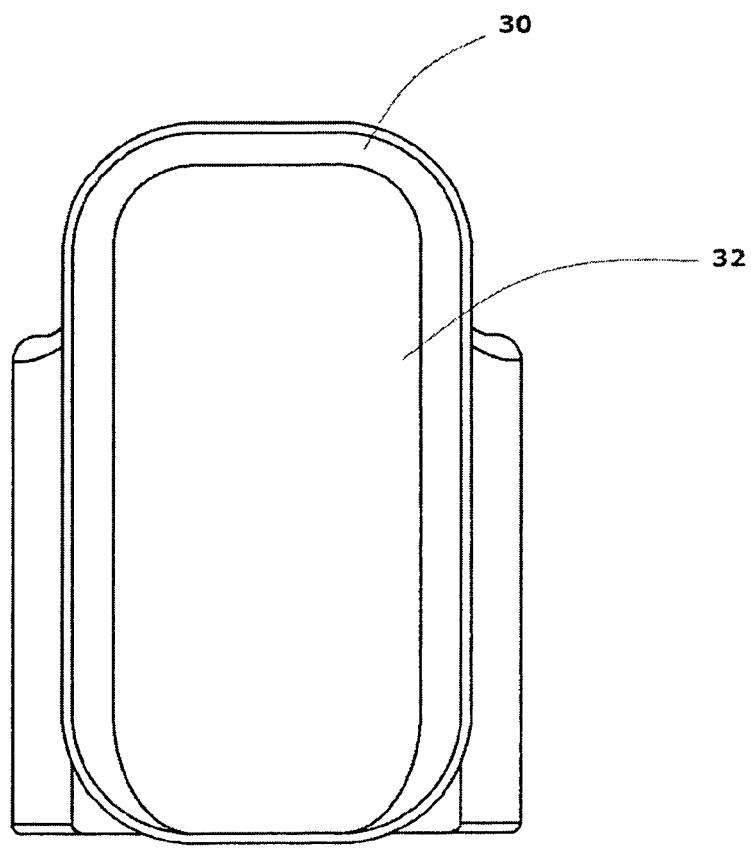
FIG. 5 is a top side view of the hand assist device, wherein a top side of an ergonomic component comprised on the device is shown.
Figure 6:
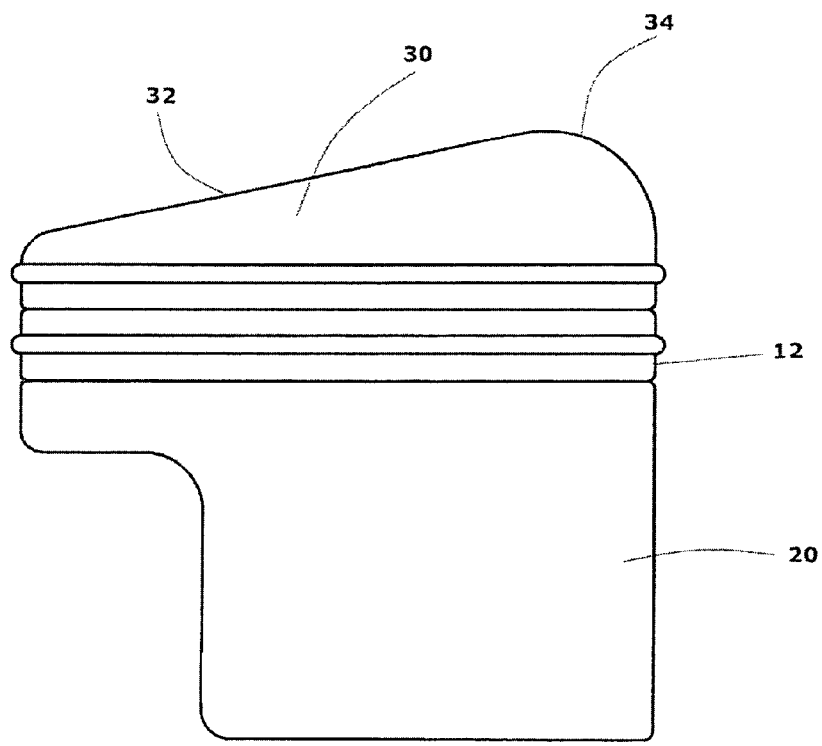
FIG. 6 is a side view of the hand assist device.

A topside view of an ergonomic component 30 is shown in FIG. 5. The ergonomic component 30 to the hand assist device 10 is permanently affixed to the center plate 12. The ergonomic component 30 is designed to comfortably fill a gap, i.e., consume a space, made between the palm and the grip portion of the endoscope. The ergonomic component 30 lifts across the entire length of the center plate 12 at an approximate 12° angle off of a vertical centerline. As shown in FIG. 6, the topside 32 of the ergonomic component 30 inclines to crest at a smooth, rounded apex 34 near the opposing end of the plate 12.

An underside 36 of the ergonomic component 30 comprises a same plurality of depressions 18 that mate with the plurality of studs 22 on the top side 14 of the center plate 12. In an alternate embodiment, however, the ergonomic component 30 can be directly and permanently affixed to the attachment mechanism 20 without a use of a center plate 12. Studs 22 on the upper side of the attachment mechanism 20 mate with the depressions 18 on the underside 36 of the ergonomic component 30. It is preferred that the center plate 12 provides an additional benefit of a ½-inch clearance to the top of the hand assist device 10. The ergonomic component 30 thus reaches the thenar crease of the palm more comfortably.

Figure 7:
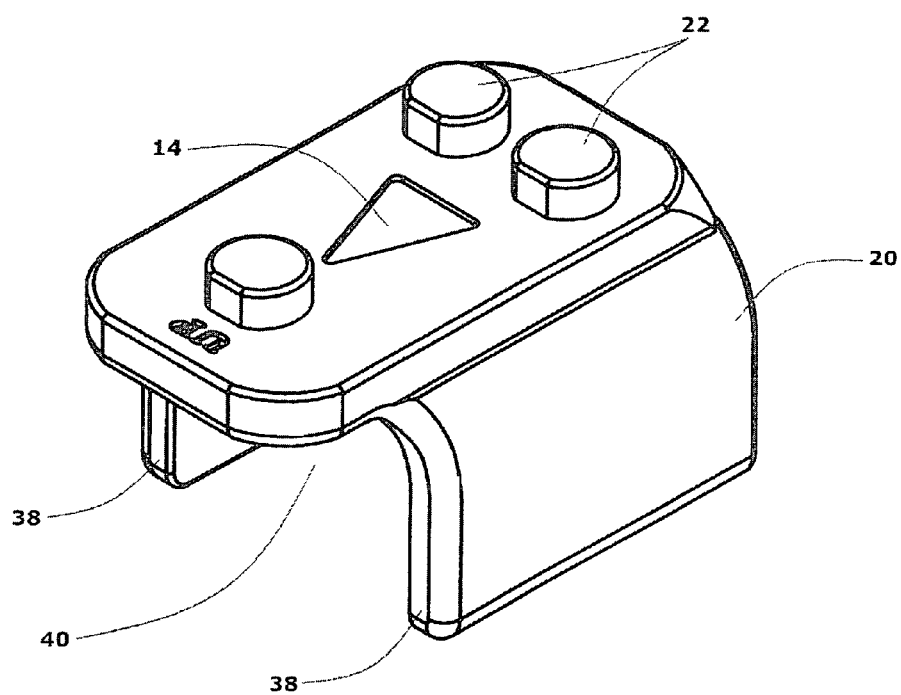
FIG. 7 is an attachment mechanism comprised on the hand assist device.

The attachment mechanism 20, as shown in FIG. 7, is provided as a means to removably secure the hand assist device 10 to an endoscope. The attachment mechanism 30 essentially comprises two approximately parallel arms 38 that extend outwards from an underside of the hand assist device 10. The two arms 38 form a channel 40 having a width and a dimension that approximates that of the grip section on the control portion of the endoscope. In this manner, the arms wrap around at least a great portion of the sidewall of the grip section so that the hand device securely affixes thereon.

Figure 8:
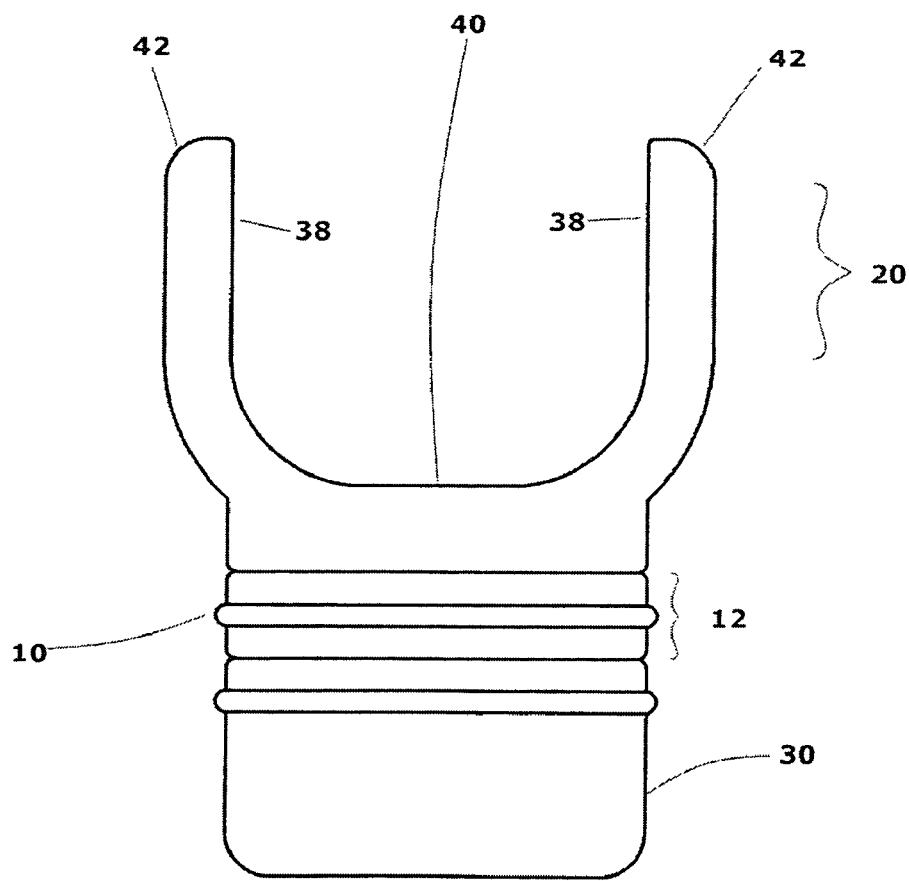
FIG. 8 is a front side view of the hand assist device shown in FIG. 2.
Figure 9:
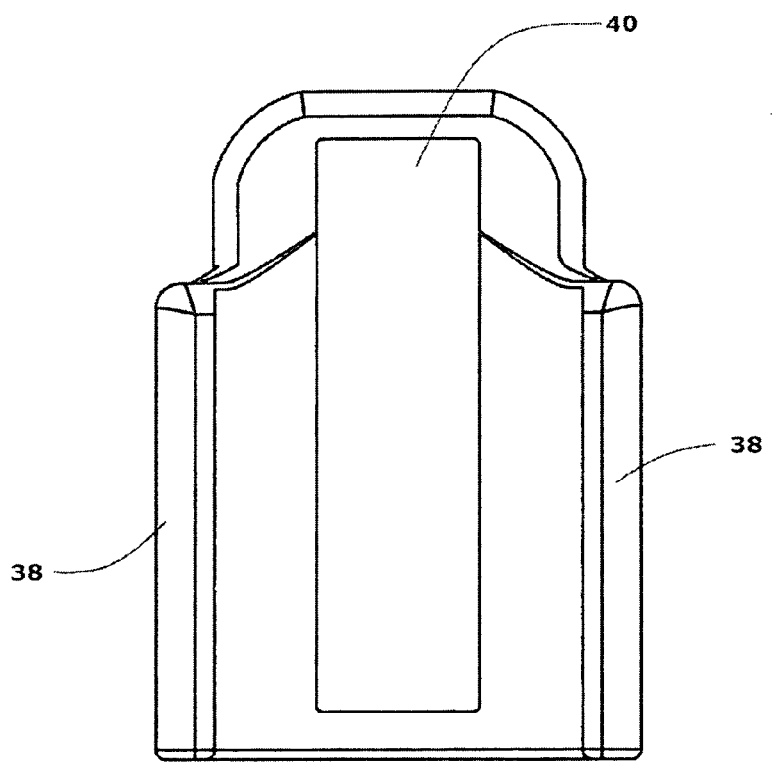
FIG. 9 is an underside view of the hand assist device shown in FIG. 2.

The arms 38 extend from an underside in a manner that is not directly perpendicular to the plane of the center plate 12. Rather, each arm softly, concavely curves inward at their opposing distal ends 42, as shown in FIGS. 8 and 9, such that they meet to form one connected body. It is anticipated that they curve to form a channel 40 that matches the curvature of the grip section on the endoscope.

It is further envisioned that the attachment mechanism 20 is used to removably snap the hand assist device 10 onto the endoscope, wherein it is held securely in place by means of an interference fit; however, the channel 40 is a pocket that can contain an adhesive tape that additionally secures the device 10 to the endoscope.

It is essential that the present hand assist device 10 be manufactured from materials that are compatible with standard sterilization and disinfection processes.

2. Operation of the Preferred Embodiment

To operate the present endoscope ergonomic hand assist device 10, the channel on the device is snapped onto the grip portion of the endoscope.

Figure 10:
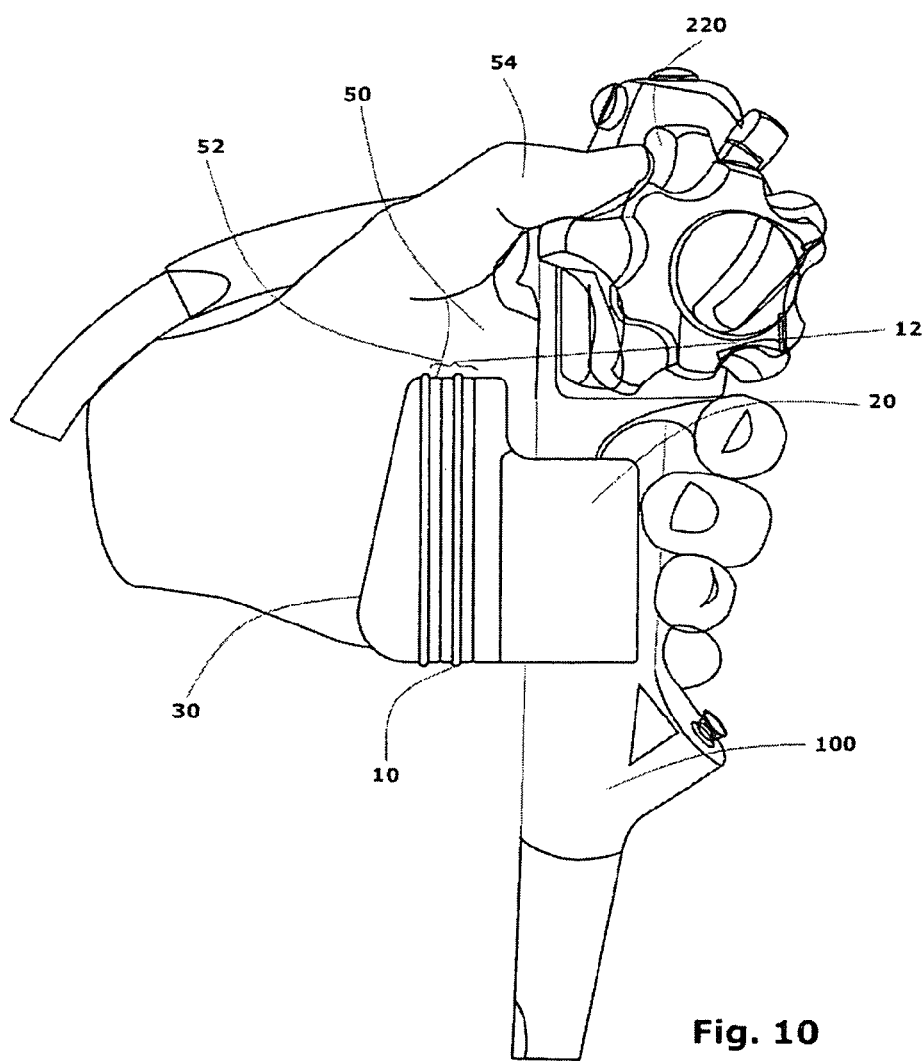
FIG. 10 is the hand assist device of FIG. 2 shown in working use.

FIG. 10 more clearly shows the ergonomic component 30 when the hand assist device 10 is in a working position. The entire palm 50 remains in one plane to the thenar crease 52. At the thenar crease 52, the thumb 54 reaches towards angulation control knobs 220 to manipulate the endoscope 100. The reach causes the entire thumb finger 54 to extend at an angle that approximates that of the ergonomic component 30. A side of the hand assist device (not shown) travels along the planar portion of the palm 50 while the ergonomic component 30 travels along the part of the palm that angles from the thenar crease 52. Essentially, the flexor tendon of the thumb 54 rests on and is comfortably supported by the ergonomic component 30 from the radial side of the hand.

The foregoing descriptions of specific embodiments of the present invention are presented for the purposes of illustration and description. They are neither intended to be exhaustive nor to limit the invention to the precise forms disclosed and, obviously, many modifications and variations are possible in light of the above teaching. The embodiments are chosen and described in order to best explain the principles of the invention and its practical application, to thereby enable others skilled in the art to best utilize the invention and the various embodiments with various modifications as are suited to the particular use contemplated. It is intended that the scope of the invention be defined by the Claims appended hereto and their equivalents. Therefore, the scope of the invention is to be limited only by the following claims.

Having thus described the invention what is claimed as new and desired to be secured by Letters Patent is as follows:

1. An endoscope ergonomic hand assist device, said hand assist device comprises:

an attachment mechanism, said attachment mechanism is provided as a means to removably secure said hand assist device to an endoscope; and, an ergonomic component, said ergonomic component adapted to till a space made between a palm and a grip portion of said endoscope;

wherein a top side of said attachment mechanism comprises at least one stud;

wherein a bottom side of said ergonomic component comprises at least one depression; and a center plate sandwiched between said attachment mechanism and said ergonomic component, said center plate provides an approximate ½-inch clearance to a top of said hand assist device so that said ergonomic component thus reaches the thenar crease of said palm;

wherein a top side of said center plate comprises at least one stud and a bottom side of said plate comprises at least one depression.

2. The hand assist device of claim 1, wherein said at least one stud on a top side of said center plate mates with said at least one depression on said ergonomic component to affix the two, said at least one stud on said attachment mechanism mates with said at least one depression on said center plate to permanently affix the two.

3. The hand assist device of claim 1, wherein said ergonomic component lilts across an entire length of the center plate to crest at a smooth, rounded apex near an opposing end at said center plate.

4. The hand assist device of claim 3, wherein said ergonomic component lifts at an approximate 12° angle off of a vertical centerline.

5. The hand assist device of claim 1, wherein said attachment mechanism comprises two approximately parallel arms that extend outwards from an underside of the hand assist device, said two arms form a channel having a width and a dimension corresponding to that of said grip portion on a control portion of said endoscope.

6. The hand assist device of claim 5, wherein said arms extend from said underside in a manner that is not directly perpendicular to a vertical plane of said ergonomic component, each of said arms softly curve inward at their opposing distal ends to meet and form one connected body.

7. The hand assist device of claim 6, wherein said arms curve to form said channel that matches a curvature of said grip portion on said endoscope.

8. The hand assist device of claim 1, wherein said attachment mechanism is used to removably snap said hand assist device onto said endoscope, wherein it is held securely in place by means of an interference fit.

9. The hand assist device of claim 8, further comprising an adhesive tape in a channel formed by arms on said attachment mechanism.

10. The hand assist device of claim 1, wherein said ergonomic component, said attachment mechanism and said center plate are all manufactured from materials that are compatible with standard sterilization and disinfection processes.

* * * * *